United States Patent [19]

Oikawa

[11] Patent Number: 5,179,583
[45] Date of Patent: Jan. 12, 1993

[54] X-RAY TUBE FOR CT APPARATUS

[75] Inventor: Shiro Oikawa, Shiga, Japan

[73] Assignee: Shimadzu Corporation, Kyoto, Japan

[21] Appl. No.: 693,267

[22] Filed: Apr. 30, 1991

[30] Foreign Application Priority Data

Apr. 30, 1990 [JP] Japan .................. 2-113999

[51] Int. Cl.⁵ .............................. H01J 35/06
[52] U.S. Cl. ..................... 378/135; 378/10; 378/136
[58] Field of Search ............ 378/10, 15, 119, 121, 378/131, 132, 134, 135, 136, 143, 144

[56] References Cited

U.S. PATENT DOCUMENTS

| | | | |
|---|---|---|---|
| 4,300,051 | 11/1981 | Little | 378/10 |
| 4,417,171 | 11/1983 | Schmitmann | 378/132 |
| 4,821,305 | 4/1989 | Anderson | 378/136 |

FOREIGN PATENT DOCUMENTS

| | | | |
|---|---|---|---|
| 0187020 | 7/1986 | European Pat. Off. | |
| 2328280 | 5/1977 | France | 378/10 |
| 2384415 | 10/1978 | France | |
| 55-129043 | 10/1980 | Japan | |
| 56-22036 | 3/1981 | Japan | |
| 58-115738 | 7/1983 | Japan | |
| WO80/00754 | 4/1980 | World Int. Prop. O. | |

Primary Examiner—David P. Porta
Attorney, Agent, or Firm—Nikaido, Marmelstein, Murray & Oram

[57] ABSTRACT

An X-ray tube for a CT apparatus comprises a ring-shaped vacuum tube containing a fixed cathode having a thermion emitting surface, a ring-shaped fixed anode, and a ring-shaped rotatable cathode interposed between the fixed cathode and fixed anode. The rotatable cathode defines a thermion receiving surface opposed to the thermion emitting surface, and a thermion emitting portion opposed to the fixed anode. Thermions are emitted from the thermion emitting portion toward the fixed anode while the rotatable cathode is suspended to non-contact state and rotated at high speed. With the thermions being accelerated and colliding on the fixed anode, an X-ray is generated toward the center of the vacuum tube. The X-ray generating position moves at high speed along a circumferential surface of the fixed anode with rotation of the rotatable cathode.

9 Claims, 6 Drawing Sheets

X-RAY TUBE FOR CT APPARATUS

BACKGROUND OF THE INVENTION (1) Field of the Invention

This invention relates to an X-ray tube for use with a CT (Computerized Tomography) apparatus, which is capable of a high-speed scan of X-ray emitting positions circumferentially of an examinee.

(2) Description of the Related Art

The X-ray CT apparatus is used to obtain images of X-ray absorptivity distribution in cross sections of an examinee by emitting X-rays from varied directions through 360 degrees (or 180 degrees) around the examinee and putting the multi-directional X-ray transmission data thereby collected to image regeneration processing. In order to collect multi-directional X-ray transmission data, the X-ray CT apparatus usually has an X-ray tube rotatable by a rotating mechanism to emit X-rays from varied directions around an examinee.

With the rotation of the X-ray tube itself, however, data cannot be collected quickly since it takes about one second for the X-ray tube to make one complete rotation or a half rotation to obtain a single slice image. The above scanning method is not fit for examination of an organ such as the heart whose movement can be grasped only with high-speed imaging in the order of 30 frames per second.

In view of the above drawback, an X-ray tube for the CT apparatus has been proposed in recent years, which is capable of running an X-ray generating position on a circumference at a very high speed. The known X-ray tube for the CT apparatus will be described hereunder with reference to FIG. 1. This X-ray tube comprises a bell-shaped vacuum tube 1, and an electron gun 2 connected to a proximal end of the vacuum tube 1. The vacuum tube 1 contains deflecting coils 3, deflecting electrodes 4, and a ring-shaped target 5. An electron beam 6 emitted from the electron gun 2 is deflected by the deflecting coils 3 and deflecting electrodes 4 to impinge on the target 5. As a result, an X-ray 7 is emitted from the target 5 toward a central part of the vacuum tube 1. By controlling the deflecting coils 3 and deflecting electrodes 4, an X-ray generating position (focal point) 8 is caused to run at high speed along the circumferential wall of the target 5. Consequently, the X-ray 7 is emitted from varied directions around an examinee M introduced into the central part of the vacuum tube 1. In this way, a picture for one frame is picked up in about 50 msec, for example.

Figure 1:
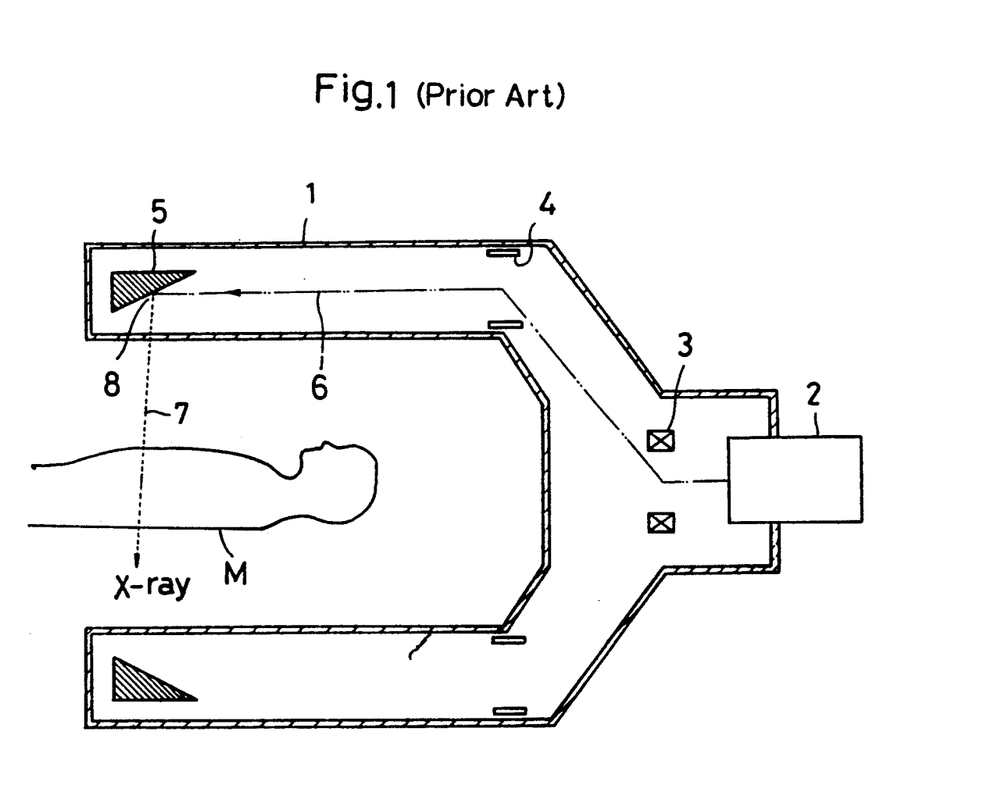
FIG. 1 is a view in vertical section showing an outline of a conventional X-ray tube for a CT apparatus.

With the known X-ray tube for the CT apparatus, however, the electron beam 6 is run in the direction perpendicular to a plane formed by the ring-shaped target 5 or by the circumference on which the X-ray generating position 8 moves, and the electron beam 6 is deflected in the course of its run. Consequently, the X-ray tube must have a very large construction about 4 meters long in the direction perpendicular to the plane formed by the ring-shaped target 5 (i.e. axially of the examinee M). An X-ray CT apparatus using such an X-ray tube requires a large installation space.

SUMMARY OF THE INVENTION

This invention has been made having regard to the state of the art noted above, and its object is to provide an X-ray tube for a CT apparatus, which is capable of a high-speed scan of X-ray generating positions circumferentially of an examinee, and yet has a compact construction having a reduced length axially of an examinee.

The above object is fulfilled, according to this invention, by an X-ray tube for a CT apparatus for scanning X-ray generating positions along a circumference of an examinee, comprising a ring-shaped vacuum tube; a fixed cathode mounted in the vacuum tube and having a first thermion emitting surface; a ring-shaped fixed anode mounted in the vacuum tube; a ring-shaped rotatable cathode having a first thermion receiving surface opposed to the first thermion emitting surface, and a thermion emitting portion opposed to the fixed anode; a lifting device for suspending the ring-shaped rotatable cathode to a non-contact state; and a driving device for rotating the ring-shaped rotatable cathode.

Specifically, the first thermion emitting surface is formed by a filament disposed on the fixed cathode. The fixed cathode may be shaped otherwise than ring-shaped as long as the first thermion emitting surface is formed opposite the first thermion receiving surface formed on the ring-shaped rotatable cathode. The thermions emitted from the first thermion emitting surface of the fixed cathode impinge on the first thermion receiving surface formed on the ring-shaped rotatable cathode. In order to reduce the difference in electric potential between the fixed cathode and rotatable cathode, it is desirable that the opposed first thermion emitting surface and thermion receiving surface have as large an area as possible, with a minimal spacing therebetween.

The thermions having entered the rotatable cathode are emitted from the thermion emitting portion of the rotatable cathode toward the fixed anode. At this time, the thermion emitting portion is heated by a suitable heating device. Specifically, a filament is mounted in the thermion emitting portion. Two examples are conceivable as means for supplying power to this filament, as follows.

Firstly, a first group of magnets is arranged, with magnetic poles thereof reversed alternately, circumferentially along an inside wall of the vacuum tube, and a first group of coils arranged circumferentially of the rotatable cathode and opposed to the first group of magnets. An electromagnetic force induced in the first group of coils when the rotatable cathode is in high-speed rotation is applied to the filament mounted in the thermion emitting portion.

In the second example, a second thermion emitting surface is formed circumferentially on the rotatable cathode and connected to one end of the filament. A second thermion receiving surface is formed opposite the second thermion emitting surface, and a DC high voltage source is provided between the second thermion receiving surface and the fixed cathode. The filament is electrically connected at the other end thereof to the first thermion receiving surface formed on the rotatable cathode. A laser beam is projected from outside the vacuum tube to the second thermion emitting surface. As a result, a current is supplied from the DC high voltage source to the filament through the second thermion receiving surface and second thermion emitting surface. In order to minimize the difference in electric potential between the second thermion emitting surface and second thermion receiving surface, it is desirable that these surfaces have as large an area as possible, with a minimal spacing therebetween.

The means for heating the thermion emitting portion of the rotatable cathode is not limited to the filament, but may comprise a laser beam directly projected to the thermion emitting portion.

The thermions emitted from the thermion emitting portion are accelerated by a high voltage electric field between the fixed anode and rotatable cathode. With impingement of the accelerated thermions on the fixed anode, an X-ray is generated from the fixed anode toward the center of the ring-shaped vacuum tube.

The ring-shaped rotatable cathode is suspended to a non-contact state when driven at high speed by the driving device to be described later. The suspending device includes, for example, a second group of magnets arranged, with magnetic poles thereof reversed alternately, circumferentially of the rotatable cathode, and a second group of coils fixed inside the vacuum tube opposite the second group of magnets.

The ring-shaped rotatable cathode is rotated by the driving device. The driving device includes, for example, a third group of magnets arranged, with magnetic poles thereof reversed alternately, circumferentially of the rotatable cathode, and at least one electromagnet disposed outwardly of the vacuum tube and opposed to the third group of magnets, with magnetic poles thereof switchable successively.

The position of the fixed anode on which the thermions emitted from the rotatable cathode and accelerated in their movement impinge moves at high speed along a circumferential surface of the fixed anode with the high-speed rotation of the rotatable cathode. As a result, the X-ray generating position runs at high speed circumferentially of the examinee introduced into the hollow center of the ring-shaped vacuum tube.

Preferably, the heat and electric charges stored in the rotatable cathode are released outwardly during a period in which X-rays are not emitted. For example, bearings may be disposed at appropriate positions on the fixed cathode and/or vacuum tube opposed to the rotatable cathode. During the period of no X-ray generation, the rotating speed of the rotatable cathode is reduced to cancel the magnetic suspension. Consequently, the rotatable cathode thermally and electrically contacts the bearings, whereby the heat and electric charges stored in the rotatable cathode are released outwardly through the bearings.

As described above, the X-ray tube for a CT apparatus according to this invention can cause the X-ray generating position to scan a circumference around an examinee at high speed since the rotatable cathode is driven to rotate at high speed as suspended to a non-contact state inside the ring-shaped vacuum tube. In addition, the ring-shaped vacuum tube has a compact construction with a reduced length axially of the examinee, which allows the CT apparatus itself that employs this vacuum tube to be reduced in size.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DESCRIPTION OF THE PREFERRED EMBODIMENTS

Preferred embodiments of this invention will be described in detail hereinafter with reference to the drawings.

First Embodiment

Figure 2:
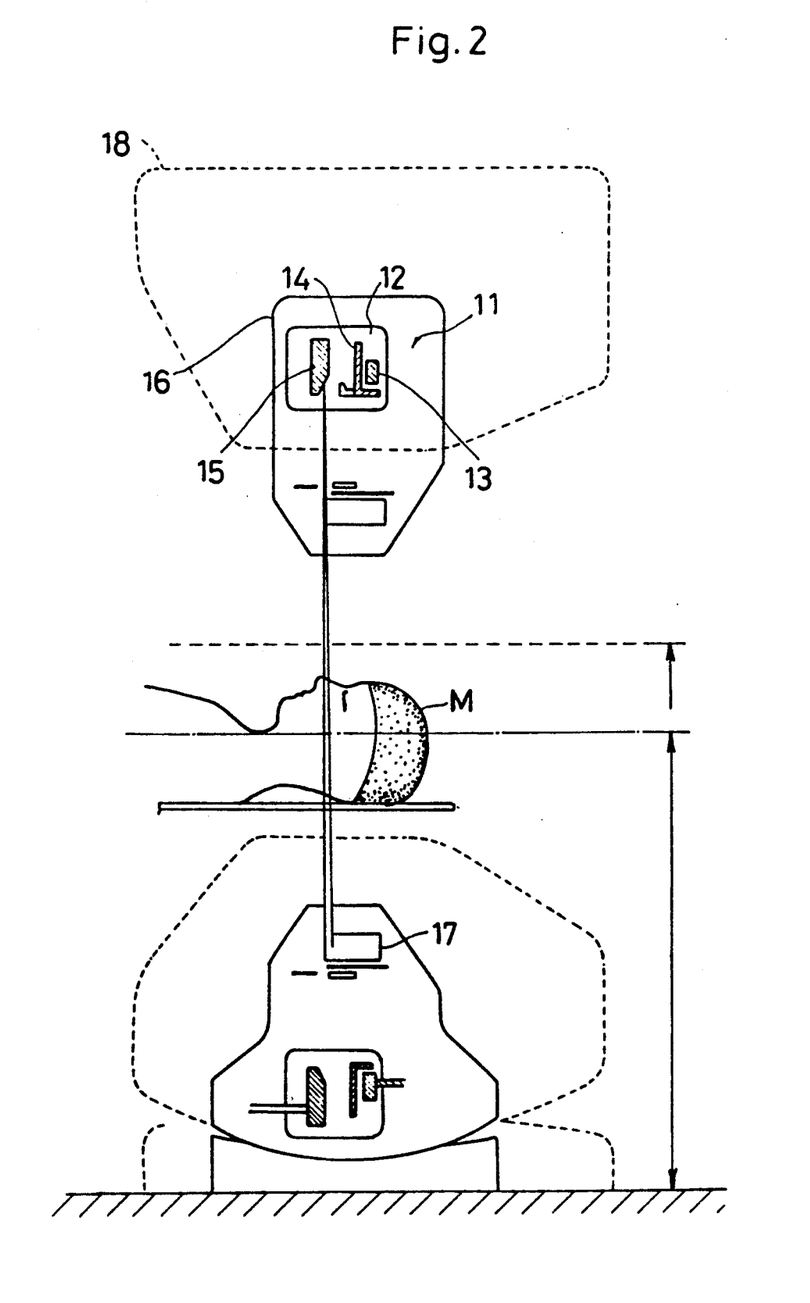
FIG. 2 is a view in vertical section showing an outline of a CT apparatus employing an X-ray tube in a first embodiment of this invention.

As shown in FIG. 2, an X-ray tube 11 for a CT apparatus in this embodiment comprises a ring-shaped vacuum tube 12 including a ring-shaped fixed cathode 13 and a ring-shaped fixed anode 15 mounted therein. A ring-shaped rotatable cathode 14 is interposed between the fixed cathode 13 and fixed anode 15 to be movable in a circumferential direction. A ring-shaped X-ray detector 17 is disposed inwardly of the X-ray tube 11. The X-ray tube 11 and detector 17 are enclosed in a ring-shaped gantry 16. The gantry 16 defines a hollow space in the center into which an examinee M is introduced with his or her body axis extending substantially perpendicular to the plane formed by the ring-shaped gantry 16.

Figure 3:
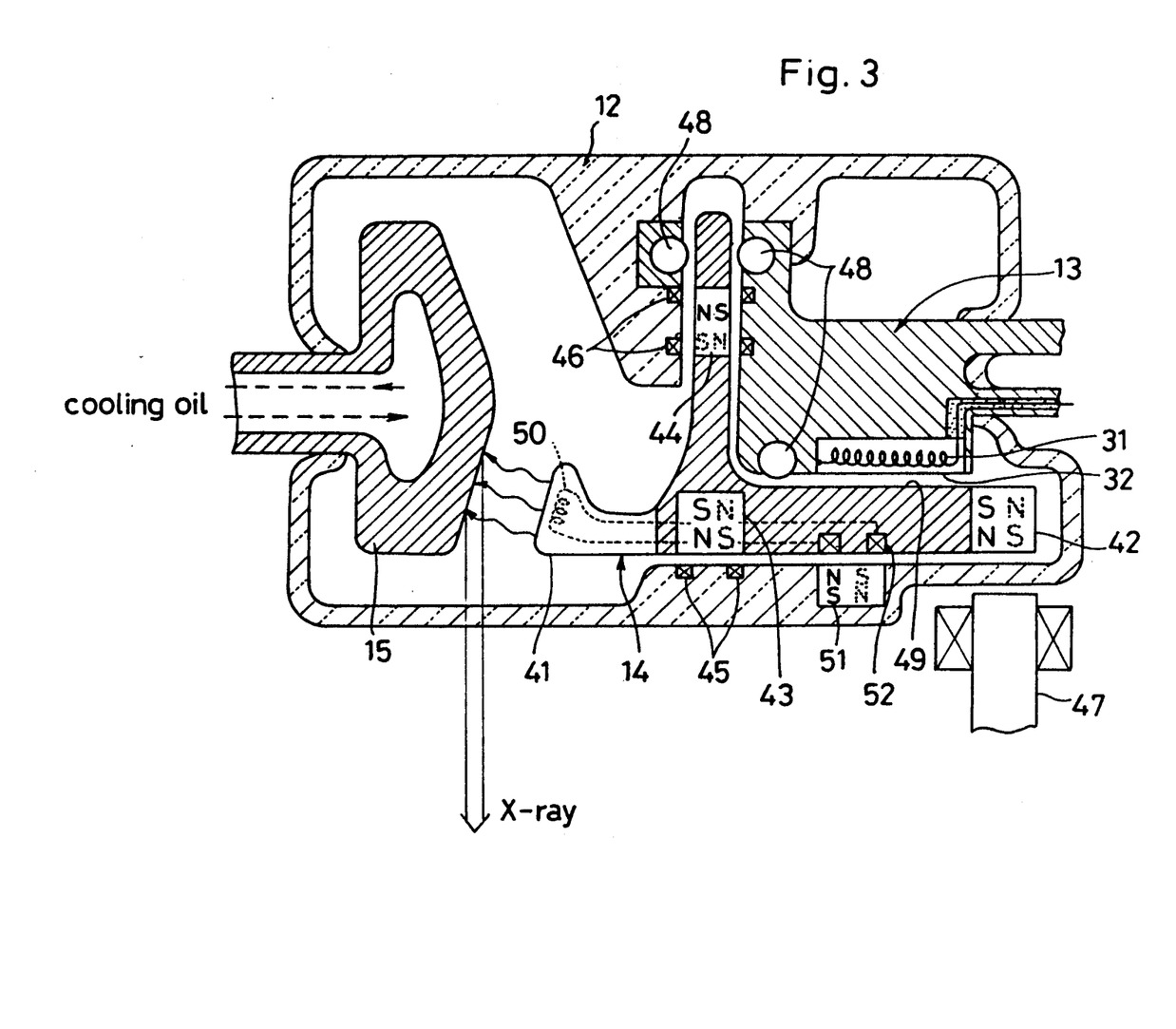
FIG. 3 is a section taken in a radial direction showing structural details of the X-ray tube shown in FIG. 2.

The vacuum tube 12, and the fixed cathode 13, rotatable cathode 14 and fixed anode 15 will be described in greater detail next. FIG. 3 is a sectional view taken radially of the vacuum tube 12. As shown in FIG. 3, the ring-shaped fixed cathode 13 includes a thermion emitting filament 31 extending over a wide range of its inside peripheral wall.

The rotatable cathode 14 includes groups of permanent magnets 43 and 44, while the vacuum tube 12 and fixed cathode 13 include groups of coils 45 and 46 arranged on inside walls thereof and opposed to the permanent magnets 43 and 44. These permanent magnets 43 and 44 and coils 45 and 46 constitute means for magnetically lifting the rotatable cathode 14 during high-speed rotation thereof. The groups of permanent magnets 43 and 44 are arranged, with magnetic poles reversed alternately, circumferentially of the rotatable cathode 14. The groups of coils 45 and 46 comprise a plurality of small coils arranged in the inside walls of the vacuum tube 12 and circumferentially of the fixed cathode 13 in opposed relations with the permanent magnets 43 and 44. When the rotatable cathode 14 rotates at high speed, electromagnetic induction generates magnetic flux which causes the coils 45 and 46 to repel the magnets 43 and 44, thereby magnetically suspending the rotatable cathode 14.

When the rotatable cathode 14 rotates at low speed, the magnetic suspending force diminishes. As a result, the rotatable cathode 14 electrically and thermally contacts, and is supported by, bearings 48 provided on the stationary vacuum tube 12 and the fixed cathode 13.

The rotatable cathode 14 further includes a group of permanent magnets 42 arranged peripherally thereof, while a plurality of electromagnets 47 are arranged outwardly of the vacuum tube 12 opposite the permanent magnets 42. These permanent magnets 42 and electromagnets 47 constitute means for rotating the rotatable cathode 14. The magnets 42 are arranged with magnetic poles reversed alternately in the circumferential direction of the rotatable cathode 14. Magnetic forces are generated between the electromagnets 47 and the group of magnets 42 by successively switching the magnetic poles of electromagnets 47, thereby rotating the rotatable cathode 14.

The fixed cathode 13 defines a thermion emitting surface 32 extending over the wide range in which the filament 31 is provided. The rotatable cathode 14 defines a thermion receiving surface 49 opposed and very close to the thermion emitting surface 32.

The rotatable cathode 14 includes an end face opposed to the fixed anode 15, from which a thermion emitting bump 41 extends to a close vicinity of the fixed anode 15. The thermion emitting bump 41 is provided for emitting, toward the fixed anode 15, a flow of electrons supplied from the fixed cathode 13 through the thermion emitting surface 32 and thermion receiving surface 49. The thermion emitting bump 41 includes a filament 50.

The vacuum tube 12 includes a group of permanent magnets 51 arranged with magnetic poles reversed alternately in the circumferential direction on the inside wall of the vacuum tube 12. The rotatable cathode 14 includes a group of coils 52 arranged in the circumferential direction thereof and opposed to the group of magnets 51. These magnets 51 and coils 52 constitute means for supplying power to the filament 50. When the rotatable cathode 14 rotates at high speed, electromagnetic induction generates an electromotive force with the group of coils 52, which is supplied to the bump 41 to heat the thermion emitting filament 50. The permanent magnets 51 may be replaced with electromagnets having magnetic poles alternately reversed in the circumferential direction. With such an arrangement of electromagnets, magnetic field intensity may be varied by controlling a current flowing through each electromagnet. Consequently, a current may be supplied to the filament 50 without relying on the rotating speed of the rotatable cathode 14.

The thermions emitted from the thermion emitting filament 50 on the rotatable cathode 14, which is maintained substantially at the same electric potential as the fixed cathode 13, are accelerated in their movement toward the fixed anode 15 maintained at high voltage. When the accelerated thermions collide on the fixed anode 15 in this condition, an X-ray is generated from a position of collision toward the examinee M. The fixed anode 15 is cooled by cooling oil circulation.

Figure 4:
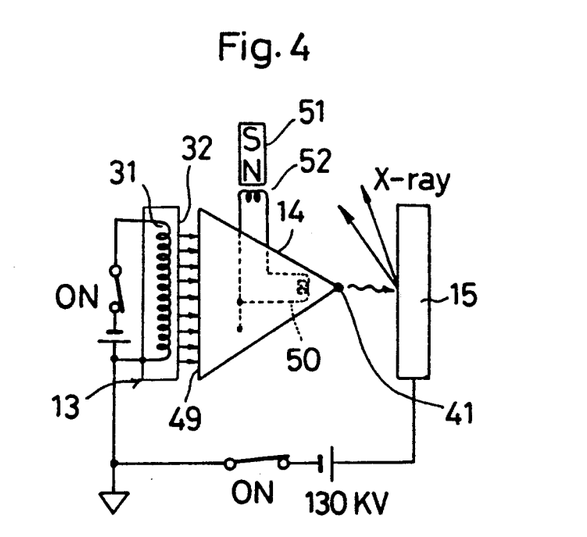
FIG. 4 is a view of an equivalent circuit of the first embodiment in an X-ray generating state.

When the rotatable cathode 14 is in high-speed rotation, the filament 31 is electrified and a high voltage is applied between the fixed cathode 13 and fixed anode 15. FIG. 4 shows an equivalent circuit in this state. The thermions generated from the filament 31 of the fixed cathode 13 are emitted from the thermion emitting surface 32, and are received by the thermion receiving surface 49 of the rotatable cathode 14. This flow of electrons is thereafter emitted from the heated thermion emitting filament 50 toward the fixed anode 15. The fixed cathode 13 has a great thermion emitting capability by virtue of the large thermion emitting surface 32. The movement of the thermions is facilitated by the large thermion emitting surface 32 and the large thermion receiving surface 49 of the rotatable cathode 14 opposed to each other with a narrow space in between.

The rotatable cathode 14 is stabilized in a state of a slightly negative electric potential relative to the fixed cathode 13. When a high voltage, e.g. 130 kV, is applied between the fixed cathode 13 and fixed anode 15, the fixed cathode 13 and rotatable cathode 14 are maintained at approximately the same electric potentials.

The rotatable cathode 14 is magnetically suspended by the groups of permanent magnets 43 and 44 and the groups of coils 45 and 46, to rotate at high speed in a non-contact state. Consequently, the X-ray generating position may be moved at high speed along a circumferential surface of the ring-shaped fixed anode 15.

Figure 5:
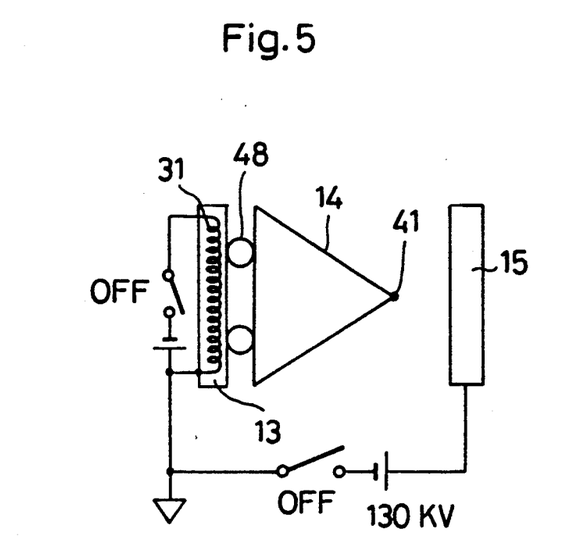
FIG. 5 is a view of an equivalent circuit of the first embodiment in a state of no X-ray generation.

The rotatable cathode 14 is rotated at a reduced speed when the power supply to the filament 31 is cut and the voltage application between the fixed cathode 13 and fixed anode 15 is discontinued to stop the X-ray generation. As a result, the magnetic forces suspending the rotatable cathode 14 diminishes to allow the rotatable cathode 14 to rest on the bearings 48. FIG. 5 shows an equivalent circuit in this state. The contact between the rotatable cathode 14 and bearings 48 allows the heat and electric charges stored in the rotatable cathode 14 during the X-ray generation to be released outwardly.

This X-ray tube 11 is flat and compact axially of the examinee since the ring-shaped vacuum tube 12 contains the ring-shaped fixed cathode 13 and ring-shaped fixed anode 15, with the ring-shaped rotatable cathode 14 interposed therebetween to be rotatable at high speed. The X-ray tube 11 is mounted along with the detector 17 in the gantry 16 which also has a compact size as a whole.

The conventional standard type CT apparatus requires a mechanism for rotating a heavy X-ray tube (about 20 kg), and therefore the gantry tends to be large (as shown in dotted lines 18 in FIG. 2). This invention has realized a compact gantry with only the rotatable cathode 14 being rotated. The gantry center where the examinee is placed has a height of about 80 cm which is a significant reduction from the height of about 95 cm in the conventional standard type CT apparatus.

Second Embodiment

Figure 6:
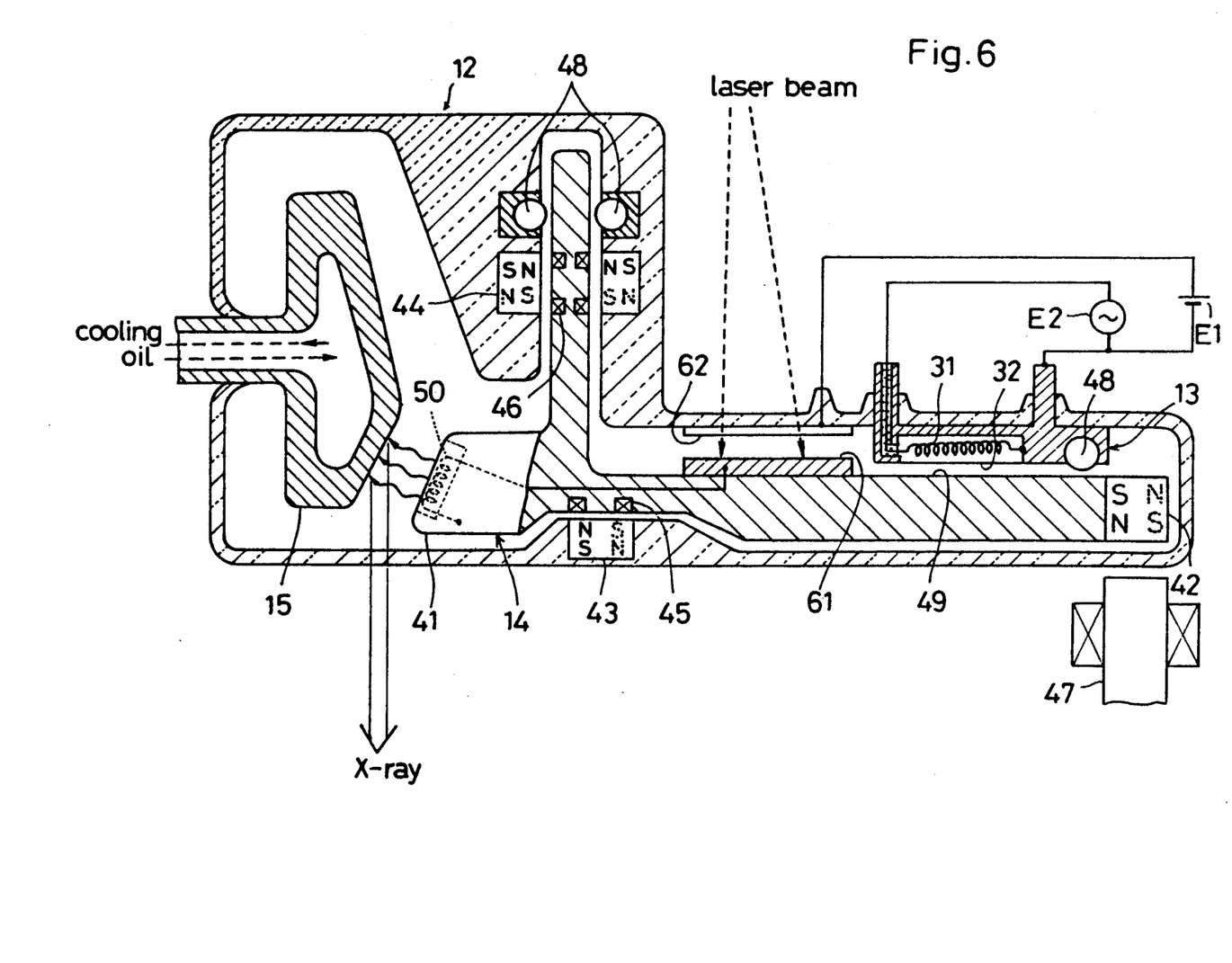
FIG. 6 is a section taken in a radial direction showing structural details of an X-ray tube in a second embodiment of this invention.

A second embodiment of this invention will be described with reference to FIG. 6. In FIG. 6, like reference numerals are used to identify like parts in FIG. 3 which are identical or similar to the components of the X-ray tube in the first embodiment and will not be described again. It is to be noted that, for magnetically suspending the rotatable cathode 14 in this embodiment, groups of permanent magnets 43 and 44 are arranged circumferentially on inside walls of the stationary vacuum tube 12, and groups of coils 45 and 46 on the rotatable cathode 14.

The characterizing feature of this embodiment lies in the power supply means for the filament 50 mounted in the thermion emitting bump 41. The rotatable cathode 14 has a thermion emitting surface 61 formed thereon and connected to one end of the filament 50 mounted in the thermion emitting bump 41. The vacuum tube 12 has a thermion receiving surface 62 fixed inside the tube 12 and opposed to the thermion emitting surface 61. The thermion receiving surface 62 is formed of a light transparent electrode. A DC high voltage source E1 is connected between the thermion receiving surface 62 and fixed cathode 13, and the other end of the filament 50 is electrically connected to the thermion receiving surface 49 formed on the rotatable cathode 14. Reference E2 in FIG. 6 denotes an AC source for electrifying the filament 31 of the fixed cathode 13.

Figure 7:
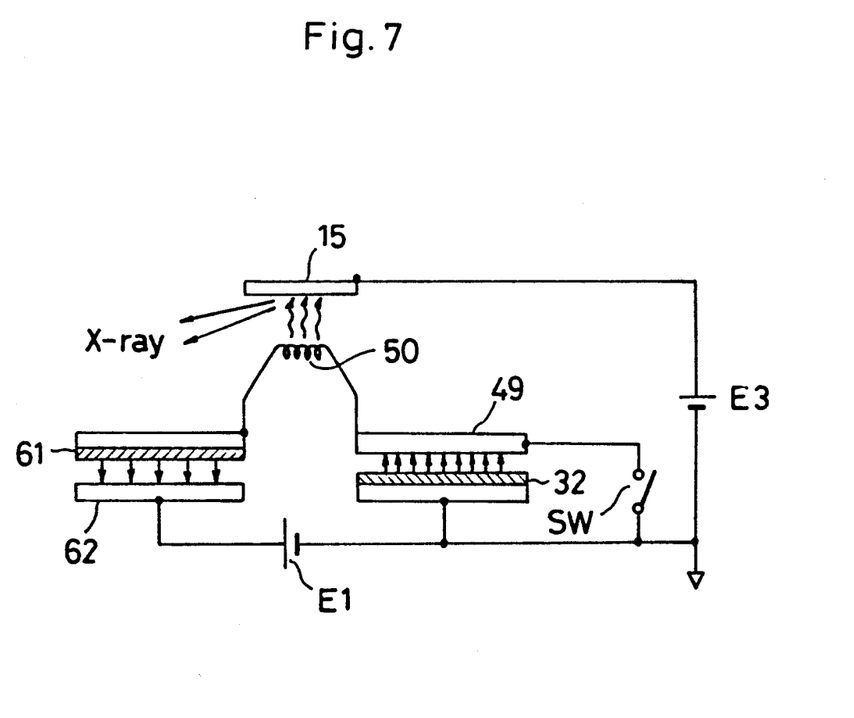
FIG. 7 is a view of an equivalent circuit of the second embodiment in an X-ray generating state.

In the X-ray tube for a CT apparatus as constructed above, a high voltage is applied between the fixed cathode 13 and fixed anode 15 while rotating the rotatable cathode 14 in the non-contact condition at high speed. At the same time, the filament 31 of the fixed cathode 13 is electrified, and a laser beam is projected from outside the vacuum tube 12 through the vacuum tube 12 and thermion receiving surface 62 to the thermion emitting surface 61. Since the thermion emitting surface 61 is provided circumferentially of the rotatable cathode 14, the laser beam constantly impinges on the thermion emitting surface 61 during the rotation of the rotatable cathode 14. This causes thermions to be emitted from the thermion emitting surface 32 of the fixed cathode 13 to the thermion receiving surface 49 of the rotatable cathode 14, and from the thermion emitting surface 61 of the rotatable cathode 14 to the thermion receiving surface 62. As a result, a circuit is formed to extend from the DC high voltage source E1 through the thermion receiving surface 62, thermion emitting surface 61, filament 50, thermion receiving surface 49, thermion emitting surface 32 and back to the DC high voltage source E1, thereby to electrify the filament 50. FIG. 7 shows an equivalent circuit in this state. Reference E3 in FIG. 7 denotes a DC high voltage source connected between the fixed cathode 13 and fixed anode 15. Reference SW schematically shows a switching operation to electrically connect the rotatable cathode 14 and fixed cathode 13, which takes place when the rotatable cathode 14 in the low speed rotation contacts the bearings 48.

With the filament 50 electrified, thermions are emitted from the thermion emitting bump 41 toward the fixed anode 15. When the thermions collide on the fixed anode 15, an X-ray is generated toward the center of the vacuum tube 12. The X-ray generating position moves at high speed in the circumferential direction with the high-speed rotation of the rotatable cathode 14. This function is the same as in the first embodiment.

The present invention may be embodied in other specific forms without departing from the spirit or essential attributes thereof and, accordingly, reference should be made to the appended claims, rather than to the foregoing specification, as indicating the scope of the invention.

What is claimed is:

1. An X-ray tube for a CT apparatus for scanning X-ray generating positions along a circumference of an examinee, comprising:
   a ring-shaped vacuum tube;
   a fixed cathode mounted in said vacuum tube and having a first thermion emitting surface;
   a ring-shaped fixed anode mounted in said vacuum tube;
   a ring-shaped rotatable cathode having a first thermion receiving surface opposed to said first thermion emitting surface, and a thermion emitting portion opposed to said fixed anode, said thermion emitting portion including a filament electrified in a non-contact state, said first thermion emitting surface and said thermion receiving surface forming part of a thermion supply passage for supplying thermions to said thermion emitting portion, and forming part of a circuit for applying a high voltage between said rotatable cathode and said fixed anode;
   magnetic suspending means for suspending said ring-shaped rotatable cathode to a non-contact state, and
   magnetic drive means for rotating said ring-shaped rotatable cathode.

2. An X-ray tube as claimed in claim 1, wherein said first thermion emitting surface of said fixed cathode includes a filament.

3. An X-ray tube as claimed in claim 1, further comprising power supply means for electrifying said filament included in said thermion emitting portion of said ring-shaped rotatable cathode, said power supply means including;
   a group of power supplying magnets arranged, with magnetic poles thereof reversed alternately, circumferentially inside said vacuum tube, and
   a group of power supplying coils arranged circumferentially of said rotatable cathode and opposed to said group of power supplying magnets, said group of power supplying coils being connected to said filament.

4. An X-ray tube as claimed in claim 1, further comprising power supply means for electrifying said filament included in said thermion emitting portion of said ring-shaped rotatable cathode, said power supply means including;
   a second thermion emitting surface formed circumferentially on said rotatable cathode for receiving a laser beam projected from outside said vacuum tube, said second thermion emitting surface being connected to one end of said filament,
   a second thermion receiving surface opposed to said second thermion emitting surface, and
   a DC high voltage source provided between said second thermion receiving surface and said fixed cathode,
   said filament being electrically connected at the other end thereof to said first thermion receiving surface formed on said rotatable cathode.

5. An X-ray tube as claimed in claim 1, wherein said magnetic suspending means includes a group of suspending magnets arranged, with magnetic poles thereof reversed alternately, circumferentially of said rotatable cathode, and a group of suspending coils fixed opposite said group of suspending magnets.

6. An X-ray tube as claimed in claim 1, wherein said magnetic suspending means includes a group of suspending magnets fixed, with magnetic poles thereof reversed alternately, in a ring form inside said vacuum tube, and a group of suspending coils arranged circumferentially of said rotatable cathode and opposed to said group of suspending magnets.

7. An X-ray tube as claimed in claim 1, wherein said magnetic drive means includes a group of driving magnets arranged, with magnetic poles thereof reversed alternately, circumferentially of said rotatable cathode, and at least one electromagnet disposed outwardly of said vacuum tube and opposed to said group of driving magnets, with magnetic poles thereof switchable successively.

8. An X-ray tube as claimed in claim 1, further comprising support means for electrically and thermally contacting said fixed cathode to provide support when said rotatable cathode is in low-speed rotation.

9. An X-ray tube as claimed in claim 8, wherein said support means is formed of bearings mounted in said vacuum tube and adjacent to said rotatable cathode.

* * * * *